US008580720B2

(12) United States Patent
Boutique et al.

(10) Patent No.: US 8,580,720 B2

(45) Date of Patent: Nov. 12, 2013

(54) LAUNDRY DETERGENT COMPOSITION COMPRISING A GLYCOSYL HYDROLASE AND A BENEFIT AGENT CONTAINING DELIVERY PARTICLE

(75) Inventors: Jean-Pol Boutique, Gembloux (BE); Nathalie Jean Marie-Louise Vanwyngaerden, Leuven (BE); Neil Joseph Lant, Newcastle upon Tyne (GB); Philip Frank Souter, Morpeth (GB); Eugene Steven Sadlowski, Cincinnati, OH (US); Genevieve Cagalawan Wenning, Villa Hills, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 882 days.

(21) Appl. No.: 12/341,730

(22) Filed: Dec. 22, 2008

(65) Prior Publication Data

US 2009/0176291 A1 Jul. 9, 2009

Related U.S. Application Data

(60) Provisional application No. 61/010,112, filed on Jan. 4, 2008, provisional application No. 61/114,584, filed on Nov. 14, 2008.

(51) Int. Cl.

| | |
|---|---|
| ***C11D 3/386*** | (2006.01) |
| ***C12N 9/14*** | (2006.01) |
| ***C12N 15/00*** | (2006.01) |

(52) U.S. Cl.

USPC ............................ 510/114; 435/195; 435/440

(58) Field of Classification Search

None

See application file for complete search history.

(56) References Cited

U.S. PATENT DOCUMENTS

| | | | | |
|---|---|---|---|---|
| 4,430,243 | A | 2/1984 | Bragg | |
| 5,486,303 | A | 1/1996 | Capeci et al. | |
| 5,489,392 | A | 2/1996 | Capeci et al. | |
| 5,516,448 | A | 5/1996 | Capeci et al. | |
| 5,565,422 | A | 10/1996 | Del Greco et al. | |
| 5,569,645 | A | 10/1996 | Dinniwell et al. | |
| 5,574,005 | A | 11/1996 | Welch et al. | |
| 5,576,282 | A | 11/1996 | Miracle et al. | |
| 5,595,967 | A | 1/1997 | Miracle et al. | |
| 5,597,936 | A | 1/1997 | Perkins et al. | |
| 5,691,297 | A | 11/1997 | Nassano et al. | |
| 5,879,584 | A | 3/1999 | Bianchetti et al. | |
| 6,225,464 | B1 | 5/2001 | Hiler, II et al. | |
| 6,268,197 | B1 | 7/2001 | Schulein et al. | |
| 6,306,812 | B1 | 10/2001 | Perkins et al. | |
| 6,326,348 | B1 | 12/2001 | Vinson et al. | |
| 6,544,926 | B1 | 4/2003 | Bodmer et al. | |
| 6,592,990 | B2 | 7/2003 | Schwantes | |
| 6,815,192 | B2 * | 11/2004 | Schnorr et al. | 435/210 |
| 6,869,923 | B1 | 3/2005 | Cunningham et al. | |
| 7,172,891 | B2 | 2/2007 | Rey et al. | |
| 7,361,736 | B2 | 4/2008 | Schnorr et al. | |
| 2002/0137657 | A1 * | 9/2002 | Lant et al. | 510/446 |
| 2003/0022807 | A1 | 1/2003 | Wilting et al. | |
| 2005/0276831 | A1 * | 12/2005 | Dihora et al. | 424/401 |
| 2007/0202063 | A1 * | 8/2007 | Dihora et al. | 424/70.1 |
| 2008/0139442 | A1 | 6/2008 | Lang | |
| 2009/0036641 | A1 | 2/2009 | Lang et al. | |

FOREIGN PATENT DOCUMENTS

| | | | |
|---|---|---|---|
| WO | WO 00/32601 | A2 | 6/2000 |
| WO | WO 02/077242 | A2 | 10/2002 |
| WO | WO 2008/110318 | A2 | 9/2008 |

OTHER PUBLICATIONS

Branden et al. Introduction to Protein Structure, Garland Publishing Inc., New York, p. 247, 1991.*

Gibson, K., Anti-redeposition effects from enzymes*, Tenside Surf. Det. 36 (1999) 6, pp. 388-392, Hanser Publishers, München.

Henrissat, Bernard, A Classification of Glycosyl Hydrolases Based on Amino Acid Sequence Similarities, Biochem. J., 1991, pp. 309-316, vol. 280.

Needleman, Saul B., et al., A General Method Applicable to the Search for Similarities in the Amino Acid Sequence of Two Proteins, J. Mol. Biol., 1970, pp. 443-453, vol. 48.

Rice, Peter, et al., EMBOSS: The European Molecular Biology Open Software Suite, Jun. 2000, pp. 276-277, vol. 16, No. 6.

ASTM Designation: B 923-02, Standard Test Method for Metal Powder Skeletal Density by Helium or Nitrogen Pycnometry, ASTM International, 2008.

ASTM Designation: D 1480-02, Standard Test Method for Density and Relative Density (Specific Gravity) of Viscous Materials by Bingham Pycnometer, ASTM International, 2003.

Sun, G., et al., Mechanical Properties of Melamine-Formaldehyde Microcapsules, Journal of Microencapsulation, 2001, pp. 593-602, vol. 18, No. 5.

Leo, Albert J., Methods of Calculating Partition Coefficients, Comprehensive Medicinal Chemistry, 1990, p. 295, vol. 4, Pergamon Press.

ASTM Designation: D 2887-04a, Standard Test Method for Boiling Range Distribution of Petroleum Fractions by Gas Chromatography, ASTM International, 2004.

* cited by examiner

*Primary Examiner* — Yong Pak

(74) *Attorney, Agent, or Firm* — Melissa G. Krasovec; Steven W. Miller

(57) ABSTRACT

The present invention relates to a laundry detergent composition comprising a glycosyl hydrolase and a benefit agent containing delivery particles, compositions comprising said particles, and processes for making and using the aforementioned particles and compositions.

8 Claims, No Drawings

LAUNDRY DETERGENT COMPOSITION COMPRISING A GLYCOSYL HYDROLASE AND A BENEFIT AGENT CONTAINING DELIVERY PARTICLE

CROSS-REFERENCE TO RELATED APPLICATIONS

This application claims the benefit of U.S. Provisional Application No. 61/010,112 filed 4 Jan. 2008; and U.S. Provisional Application No. 61/114,584 filed 14 Nov. 2008.

FIELD OF INVENTION

The present application relates to a laundry detergent composition comprising a glycosyl hydrolase and a benefit agent containing delivery particle.

BACKGROUND OF THE INVENTION

Benefit agents, such as perfumes, silicones, waxes, vitamins and fabric softening agents, are expensive and generally less effective when employed at high levels in fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

Accordingly, there is a need for a composition that provides improved benefit agent delivery efficiency.

SUMMARY OF THE INVENTION

The present invention relates to a laundry detergent composition comprising a glycosyl hydrolase and a benefit agent containing delivery particles comprising a core material and a wall material that at least partially surrounds the core material. Without wishing to be bound by theory the Inventors believe that the action of certain glycosyl hydrolase on the fabric surface opens up the pore structure of the cotton fibres so as to increase the entrapment of the benefit agent containing particles in the fabric. In addition, the action of these certain glycosyl hydrolases increases the surface area of the fabric, further improving the performance of the benefit agent during the laundering process.

DETAILED DESCRIPTION OF THE INVENTION

Glycosyl Hydrolase

The glycosyl hydrolase has enzymatic activity towards both xyloglucan and amorphous cellulose substrates, wherein the glycosyl hydrolase is selected from GH families 5, 12, 44 or 74.

The enzymatic activity towards xyloglucan substrates is described in more detail below. The enzymatic activity towards amorphous cellulose substrates is described in more detail below.

The glycosyl hydrolase enzyme preferably belongs to glycosyl hydrolase family 44. The glycosyl hydrolase (GH) family definition is described in more detail in Biochem J. 1991, v280, 309-316.

The glycosyl hydrolase enzyme preferably has a sequence at least 70%, or at least 75% or at least 80%, or at least 85%, or at least 90%, or at least 95% identical to sequence ID No. 1.

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

Suitable glycosyl hydrolases are selected from the group consisting of: GH family 44 glycosyl hydrolases from *Paenibacillus polyxyma* (wild-type) such as XYG1006 described in WO 01/062903 or are variants thereof; GH family 12 glycosyl hydrolases from *Bacillus licheniformis* (wild-type) such as Seq. No. ID: 1 described in WO 99/02663 or are variants thereof; GH family 5 glycosyl hydrolases from *Bacillus agaradhaerens* (wild type) or variants thereof; GH family 5 glycosyl hydrolases from *Paenibacillus* (wild type) such as XYG1034 and XYG 1022 described in WO 01/064853 or variants thereof; GH family 74 glycosyl hydrolases from *Jonesia* sp. (wild type) such as XYG1020 described in WO 2002/077242 or variants thereof; and GH family 74 glycosyl hydrolases from *Trichoderma Reesei* (wild type), such as the enzyme described in more detail in Sequence ID no. 2 of WO03/089598, or variants thereof.

Preferred glycosyl hydrolases are selected from the group consisting of: GH family 44 glycosyl hydrolases from *Paenibacillus polyxyma* (wild-type) such as XYG1006 or are variants thereof.

Enzymatic Activity Towards Xyloglucan Substrates

An enzyme is deemed to have activity towards xyloglucan if the pure enzyme has a specific activity of greater than 50000 XyloU/g according to the following assay at pH 7.5.

The xyloglucanase activity is measured using AZCL-xyloglucan from Megazyme, Ireland as substrate (blue substrate).

A solution of 0.2% of the blue substrate is suspended in a 0.1M phosphate buffer pH 7.5, 20° C. under stirring in a 1.5 ml Eppendorf tubes (0.75 ml to each), 50 microliters enzyme solution is added and they are incubated in an Eppendorf Thermomixer for 20 minutes at 40° C., with a mixing of 1200 rpm. After incubation the coloured solution is separated from the solid by 4 minutes centrifugation at 14,000 rpm and the absorbance of the supernatant is measured at 600 nm in a 1 cm cuvette using a spectrophotometer. One XyloU unit is defined as the amount of enzyme resulting in an absorbance of 0.24 in a 1 cm cuvette at 600 nm.

Only absorbance values between 0.1 and 0.8 are used to calculate the XyloU activity. If an absorbance value is measured outside this range, optimization of the starting enzyme concentration should be carried out accordingly.

Enzymatic Activity Towards Amorphous Cellulose Substrates

An enzyme is deemed to have activity towards amorphous cellulose if the pure enzyme has a specific activity of greater than 20000 EBG/g according to the following assay at pH 7.5. Chemicals used as buffers and substrates were commercial products of at least reagent grade.

Endoglucanase Activity Assay Materials:

0.1M phosphate buffer pH 7.5

Cellazyme C tablets, supplied by Megazyme International, Ireland.

Glass microfiber filters, GF/C, 9 cm diameter, supplied by Whatman.

Method:

In test tubes, mix 1 ml pH 7.5 buffer and 5 ml deionised water.

Add 100 microliter of the enzyme sample (or of dilutions of the enzyme sample with known weight:weight dilution factor). Add 1 Cellazyme C tablet into each tube, cap the tubes and mix on a vortex mixer for 10 seconds. Place the tubes in a thermostated water bath, temperature 40° C.

After 15, 30 and 45 minutes, mix the contents of the tubes by inverting the tubes, and replace in the water bath. After 60 minutes, mix the contents of the tubes by inversion and then filter through a GF/C filter. Collect the filtrate in a clean tube.

Measure Absorbance (Aenz) at 590 nm, with a spectrophotometer. A blank value, Awater, is determined by adding 100 μl water instead of 100 microliter enzyme dilution.

Calculate $A$delta=$A$enz−$A$water.

Adelta must be <0.5. If higher results are obtained, repeat with a different enzyme dilution factor. Determine DFO.1, where DFO.1 is the dilution factor needed to give Adelta=0.1.

Unit Definition: 1 Endo-Beta-Glucanase activity unit (1 EBG) is the amount of enzyme that gives Adelta=0.0, under the assay conditions specified above. Thus, for example, if a given enzyme sample, after dilution by a dilution factor of 100, gives Adelta=0.10, then the enzyme sample has an activity of 100 EBG/g.

Benefit Agent Containing Delivery Particle

The Inventors discovered that the problem of achieving effective and efficient benefit agent delivery can be solved in an economical manner when a benefit agent containing delivery particle having a certain combination of physical and chemical characteristics is incorporated in a laundry detergent composition that additionally comprises a glycosyl hydrolase. Such physical and chemical characteristics are defined by the following parameters: particle size coefficient of variation, fracture strength, benefit agent retention ratio and average particle size. Such parameters may be combined to yield a Delivery Index.

In one aspect, the particle comprises a core material and a wall material that at least partially surrounds the core material, said particle having a Delivery Index of at least about 0.05, at least about 7, or at least about 70.

In one aspect, the particle comprises a core material and a wall material that at least partially surrounds the core material, said particle having:

a.) a particle size coefficient of variation of from about 1.5 to about 6.0, from about 2.0 to about 3.5, or even from about 2.5 to about 3.2;

b.) a fracture strength of from about 0.1 psia to about 110 psia, from about 1 to about 50 psia, or even from about 4 to about 16 psia;

c.) a benefit agent retention ratio of from about 2 to about 10, from about 30 to about 90, or even from about 40 to about 70; and d.) an average particle size of from about 1 micron to about 100 microns, from about 5 microns to about 80 microns, or even from about 15 microns to about 50 microns.

In one aspect of the present invention, said particle may have and/or comprise any combination of the parameters described in the present specification.

Useful wall materials include materials selected from the group consisting of polyethylenes, polyamides, polystyrenes, polyisoprenes, polycarbonates, polyesters, polyacrylates, polyureas, polyurethanes, polyolefins, polysaccharides, epoxy resins, vinyl polymers, and mixtures thereof. In one aspect, useful wall materials include materials that are sufficiently impervious to the core material and the materials in the environment in which the benefit agent containing delivery particle will be employed, to permit the delivery benefit to be obtained. Suitable impervious wall materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In one aspect, the wall material comprises melamine cross-linked with formaldehyde.

Useful core materials include perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. In one aspect, said perfume raw material is selected from the group consisting of alcohols, ketones, aldehydes, esters, ethers, nitriles alkenes. In one aspect the core material comprises a perfume. In one aspect, said perfume comprises perfume raw materials selected from the group consisting of alcohols, ketones, aldehydes, esters, ethers, nitriles alkenes and mixtures thereof. In one aspect, said perfume may comprise a perfume raw material selected from the group consisting of perfume raw materials having a boiling point (B.P.) lower than about 250° C. and a C log P lower than about 3, perfume raw materials having a B.P. of greater than about 250° C. and a C log P of greater than about 3, perfume raw materials having a B.P. of greater than about 250° C. and a C log P lower than about 3, perfume raw materials having a B.P. lower than about 250° C. and a C log P greater than about 3 and mixtures thereof. Perfume raw materials having a boiling point B.P. lower than about 250° C. and a C log P lower than about 3 are known as Quadrant I perfume raw materials, perfume raw materials having a B.P. of greater than about 250° C. and a C log P of greater than about 3 are known as Quadrant IV perfume raw materials, perfume raw materials having a B.P. of greater than about 250° C. and a C log P lower than about 3 are known as Quadrant II perfume raw materials, perfume raw materials having a B.P. lower than about 250° C. and a C log P greater than about 3 are known as a Quadrant III perfume raw materials. In one aspect, said perfume comprises a perfume raw material having B.P. of lower than about 250° C. In one aspect, said perfume comprises a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

In one aspect, said perfume comprises a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

The perfume raw materials and accords may be obtained from one or more of the following companies Firmenich (Geneva, Switzerland), Givaudan (Argenteuil, France), IFF (Hazlet, N.J.), Quest (Mount Olive, N.J.), Bedoukian (Danbury, Conn.), Sigma Aldrich (St. Louis, Mo.), Millennium Specialty Chemicals (Olympia Fields, Ill.), Polarone International (Jersey City, N.J.), Fragrance Resources (Keyport, N.J.), and Aroma & Flavor Specialties (Danbury, Conn.).

Process of Making Benefit Agent Containing Delivery Particles

The particle disclosed in the present application may be made via the teachings of U.S. Pat. No. 6,592,990 B2 and/or U.S. Pat. No. 6,544,926 B1 and the examples disclosed herein.

Laundry Detergent Composition

The laundry detergent composition comprises: (a) a glycosyl hydrolase having enzymatic activity towards both xyloglucan and amorphous cellulose substrates, wherein the glycosyl hydrolase is selected from GH families 5, 12, 44 or 74; (b) a particle comprising a core material and a wall material that surrounds the core material, said particle preferably having a Delivery Index of at least about 0.05 said composition being a consumer product; and (c) detersive surfactant.

While the precise level of particle (b) that is employed depends on the type and end use of the composition, a composition may comprise from about 0.01 to about 10, from about 0.1 to about 10, or even from about 0.2 to about 5 weight % of said particle based on total composition weight. In one aspect, a cleaning composition may comprise, from about 0.1 to about 1 weight % of such particle based on total composition weight of such particle. In one aspect, a fabric treatment composition may comprise, based on total fabric treatment composition weight, form about 0.01 to about 10% of such particle.

Aspects of the invention include the use of the particles of the present invention in laundry detergent compositions (e.g., TIDE™). The compositions disclosed herein are typically formulated such that, during use in aqueous cleaning operations, the wash water will have a pH of between about 6.5 and about 12, or between about 7.5 and 10.5.

Laundry detergent compositions disclosed herein typically comprise a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

The composition is preferably in the form of a liquid. The composition typically comprises adjunct materials. The adjunct materials are described in more detail below.

The composition can be in any form. The composition may in the form of a liquid or solid. The composition is preferably in the form of a liquid. The composition may be at least partially, preferably completely, enclosed by a water-soluble film.

Solid Laundry Detergent Composition

In one embodiment of the present invention, the composition is a solid laundry detergent composition, preferably a solid laundry powder detergent composition.

The composition preferably comprises from 0 wt % to 10 wt %, or even to 5 wt % zeolite builder. The composition also preferably comprises from 0 wt % to 10 wt %, or even to 5 wt % phosphate builder.

The composition typically comprises anionic detersive surfactant, preferably linear alkyl benzene sulphonate, preferably in combination with a co-surfactant. Preferred co-surfactants are alkyl ethoxylated sulphates having an average degree of ethoxylation of from 1 to 10, preferably from 1 to 3, and/or ethoxylated alcohols having an average degree of ethoxylation of from 1 to 10, preferably from 3 to 7.

The composition preferably comprises chelant, preferably the composition comprises from 0.3 wt % to 2.0 wt % chelant. A suitable chelant is ethylenediamine-N,N'-disuccinic acid (EDDS).

The composition may comprise cellulose polymers, such as sodium or potassium salts of carboxymethyl cellulose, carboxyethyl cellulose, sulfoethyl cellulose, sulfopropyl cellulose, cellulose sulfate, phosphorylated cellulose, carboxymethyl hydroxyethyl cellulose, carboxymethyl hydroxypropyl cellulose, sulfoethyl hydroxyethyl cellulose, sulfoethyl hydroxypropyl cellulose, carboxymethyl methyl hydroxyethyl cellulose, carboxymethyl methyl cellulose, sulfoethyl methyl hydroxyethyl cellulose, sulfoethyl methyl cellulose, carboxymethyl ethyl hydroxyethyl cellulose, carboxymethyl ethyl cellulose, sulfoethyl ethyl hydroxyethyl cellulose, sulfoethyl ethyl cellulose, carboxymethyl methyl hydroxypropyl cellulose, sulfoethyl methyl hydroxypropyl cellulose, carboxymethyl dodecyl cellulose, carboxymethyl dodecoyl cellulose, carboxymethyl cyanoethyl cellulose, and sulfoethyl cyanoethyl cellulose. The cellulose may be a substituted cellulose substituted by two or more different substituents, such as methyl and hydroxyethyl cellulose.

The composition may comprise soil release polymers, such as Repel-o-Tex™. Other suitable soil release polymers are anionic soil release polymers. Suitable soil release polymers are described in more detail in WO05123835A1, WO07079850A1 and WO08110318A2.

The composition may comprise a spray-dried powder. The spray-dried powder may comprise a silicate salt, such as sodium silicate.

Adjunct Materials

Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems.

When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, other cellulases, other xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Processes of Making and Using Compositions

The compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303.

Test Methods

It is understood that the test methods that are disclosed in the Test Methods Section of the present application must be used to determine the respective values of the parameters of Applicants' invention as such invention is described and claimed herein.

(1) Particle Size Distribution a.) Place 1 gram of particles in 1 liter of distilled deionized (DI) water.

b.) Permit the particles to remain in the DI water for 10 minutes and then recover the particles by filtration.

c.) Determine the particle size distribution of the particle sample by measuring the particle size of 50 individual particles using the experimental apparatus and method of Zhang, Z.; Sun, G; "Mechanical Properties of Melamine-Formaldehyde microcapsules," J. Microencapsulation, vol 18, no. 5, pages 593-602, 2001.

d.) Average the 50 independent particle diameter measurements to obtain an average particle diameter.

e.) Use the 50 independent measurements to calculate a standard deviation of particle size using the following equation:

$$\mu = \sqrt{\frac{\sum (d-s)^2}{n-1}}$$

where
- μ is the standard deviation
- s is the average particle diameter
- d is the independent particle diameter
- n is the total number of particles whose diameter is measured.

(2) Benefit Agent Retention Ratio a.) Add 1 gram of particle to 99 grams of composition that the particle will be employed in.

b.) Age the particle containing composition of a.) above for 2 weeks at 40° C. in a sealed, glass jar.

c.) Recover the particles from b.) above by filtration.

d.) Treat the particles of c.) above with a solvent that will extract all the benefit agent from the particles.

e.) Inject the benefit agent containing solvent from d.) above into a Gas Chromatograph and integrate the peak areas to determine the total quantity of benefit agent extracted from the particle sample.

f.) This quantity is then divided by the quantity that would be present if nothing had leaked out of the microcapsule (e.g. the total quantity of core material that is dosed into the composition via the microcapsules). This value is then multiplied by the ratio of average particle diameter to average particle thickness to obtain a Benefit Agent Retention Ratio.

A detailed analytical procedure to measure the Benefit Agent Retention Ratio is:

ISTD Solution
1. Weigh out 25 mg dodecane into a weigh boat.
2. Rinse the dodecane into a 1000 mL volumetric flask using ethanol.
3. Add ethanol to volume mark.
4. Stir solution until mixed. This solution is stable for 2 months.

Calibration Standard
1. Weigh out 75 mg of core material into a 100 mL volumetric flask.
2. Dilute to volume with ISTD solution to from above. This standard solution is stable for 2 months.
3. Mix well.
4. Analyze via GC/FID.

Basic Sample Prep
(Prepare samples in triplicate)
1. Weigh 1.000 gram sample of aged composition containing particles into a 100 mL tri-pour beaker. Record weight.
2. Add 4 drops (approximately 0.1 gram) 2-ethyl-1,3-Hexanediol into the tri-pour beaker.
3. Add 50 mL Deionized water to the beaker. Stir for 1 minute.
4. Using a 60 cc syringe, filter through a Millipore Nitrocellulose Filter Membrane (1.2 micron, 25 mm diameter).
5. Rinse through the filter with 10 mL of Hexane
6. Carefully remove the filter membrane and transfer to a 20 mL scintillation vial (using tweezers).
7. Add 10 mL ISTD solution (as prepared above) to the scintillation vial containing the filter.
8. Cap tightly, mix, and heat vial at 60° C. for 30 min.
9. Cool to room temperature.
10. Remove 1 mL and filter through a 0.45-micron PTFE syringe filter into GC vial. Several PTFE filters may be required to filter a 1 mL sample aliquot.
11. Analyze via GC/FID.

GG/FID Analysis Method:

Column—30 m×0.25 mm id, 1-um DB-1 phase

GC—6890 GC equipped with EPC control and constant flow capability

Method—50° C., 1 min. hold, temperature ramp of 4° C./min. to 300° C., and hold for 10 min.

Injector—1 uL splitless injection at 240° C.

GC/FID Analysis Method—Microbore Column Method:

Column—20 m×0.1 mm id, 0.1 μm DB-5

GC—6890 GC equipped with EPC control and constant flow capability (constant flow 0.4 mL/min)

Method—50° C., no hold, temperature ramp of 16° C./min to 275° C., and hold for 3 min.

Injector—1 μL split injection (80:1 split) at 250° C.

Calculations:

$$\% \text{ Total Perfume} = \frac{A_{IS} \times W_{per\text{-}std} \times A_{per\text{-}sam}}{A_{per\text{-}std} \times A_{is\text{-}sam} \times W_{sam}} \times 100\%$$

where
- $A_{is}$=Area of internal standard in the core material calibration standard;
- $W_{per\text{-}std}$=weight of core material in the calibration sample
- $A_{per\text{-}sam}$=Area of core material peaks in the composition containing particle sample;
- $A_{per\text{-}std}$=Area of core material peaks in the calibration sample.
- $A_{is\text{-}sam}$=Area of internal standard in composition containing particle sample;
- $W_{sam}$=Weight of the composition containing particle sample $$\text{Retention\_Ratio} = \left(\frac{\text{Total\_Perfume}}{\text{Perfume\_Dosed\_Into\_Product\_Via\_Microcapsules}}\right)\left(\frac{\mu}{T}\right)$$

where
- μ is the average particle diameter, from Test Method 1
- T is the average particle thickness as calculated from Test Method 3

(3) Fracture Strength a.) Place 1 gram of particles in 1 liter of distilled deionized (DI) water.

b.) Permit the particles to remain in the DI water for 10 minutes and then recover the particles by filtration.

c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture pressure by dividing the average rupture force (in Newtons) by the average cross-sectional area (as determined by Test Method 1 above) of the spherical particle ($\pi r^2$, where r is the radius of the particle before compression).

d.) Calculate the average fracture strength by using the following equation:

$$\sigma_{fracture\_stress} = \frac{P}{4(d/T)}$$

where

P is the average fracture pressure from a.) above d is the average diameter of the particle (as determined by Test Method 1 above)

T is the average shell thickness of the particle shell as determined by the following equation:

$$T = \frac{r_{capsule}(1-c)\rho_{perfume}}{3[c\rho_{wall} + (1-c)\rho_{perfume}]}$$

where c is the average perfume content in the particle r is the average particle radius $\rho_{wall}$ is the average density of the shell as determined by ASTM method B923-02, "Standard Test Method for Metal Powder Skeletal Density by Helium or Nitrogen Pycnometry", ASTM International.

$\rho_{perfume}$ is the average density of the perfume as determined by ASTM method D1480-93(1997) "Standard Test Method for Density and Relative Density (Specific Gravity) of Viscous Materials by Bingham Pycnometer", ASTM International.

(4) C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. taylor, and C. A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A.

(5) Boiling Point

Boiling point is measured by ASTM method D2887-04a, "Standard Test Method for Boiling Range Distribution of Petroleum Fractions by Gas Chromatography," ASTM International.

(6) Delivery Index Calculation

The Delivery Index for a particle is calculated using the following equation:

$$\text{Delivery\_Index} = \frac{\left[\left(\frac{\mu}{\sigma}\right)_{Particle\_Size}\left(\frac{f_0}{f}\right)_{Fracture\_Stress}\left(\frac{L/L_0}{t/\mu}\right)\right]}{100}$$

Where $\mu$ is the average particle diameter $\sigma$ is the standard deviation of the average particle diameter $f_0$ is the minimum in-use fracture strength required to break the microcapsule f is the measured Fracture Strength $(L/L_0)/(t/\mu)$ is the Benefit Agent Retention Ratio t is the shell thickness of the particle

EXAMPLES

Examples 1-8

Liquid laundry detergent compositions suitable for front-loading automatic washing machines.

| | Composition (wt % of composition) | | | | | | | |
|---|---|---|---|---|---|---|---|---|
| Ingredient | 1 | 2 | 3 | 4 | 5 | 6 | 7 | 8 |
| Alkylbenzene sulfonic acid | 7 | 11 | 4.5 | 1.2 | 1.5 | 12.5 | 5.2 | 4 |
| Sodium $C_{12-14}$ alkyl ethoxy 3 sulfate | 2.3 | 3.5 | 4.5 | 4.5 | 7 | 18 | 1.8 | 2 |
| $C_{14-15}$ alkyl 8-ethoxylate | 5 | 8 | 2.5 | 2.6 | 4.5 | 4 | 3.7 | 2 |
| $C_{12}$ alkyl dimethyl amine oxide | — | — | 0.2 | — | — | — | — | — |
| $C_{12-14}$ alkyl hydroxyethyl dimethyl ammonium chloride | — | — | — | 0.5 | — | — | — | — |
| $C_{12-18}$ Fatty acid | 2.6 | 4 | 4 | 2.6 | 2.8 | 11 | 2.6 | 1.5 |
| Citric acid | 2.6 | 3 | 1.5 | 2 | 2.5 | 3.5 | 2.6 | 2 |
| Protease (Purafect ® Prime) | 0.5 | 0.7 | 0.6 | 0.3 | 0.5 | 2 | 0.5 | 0.6 |
| Amylase (Natalase ®) | 0.1 | 0.2 | 0.15 | — | 0.05 | 0.5 | 0.1 | 0.2 |
| Mannanase (Mannaway ®) | 0.05 | 0.1 | 0.05 | — | — | 0.1 | 0.04 | — |
| Xyloglucanase XYG1006* (mg aep/100 g detergent) | 1 | 4 | 3 | 3 | 2 | 8 | 2.5 | 4 |
| Random graft co-polymer[1] | 1 | 0.2 | 1 | 0.4 | 0.5 | 2.7 | 0.3 | 1 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 0.4 | 2 | 0.4 | 0.6 | 1.5 | 1.8 | 0.7 | 0.3 |
| Ethoxylated Polyethylenimine[2] | — | — | — | — | — | 0.5 | — | — |
| Amphiphilic alkoxylated grease cleaning polymer[3] | 0.1 | 0.2 | 0.1 | 0.2 | 0.3 | 0.3 | 0.2 | 0.3 |
| Diethoxylated poly (1,2 propylene terephthalate short block soil release polymer. | — | — | — | — | — | — | 0.3 | — |
| Diethylenetriaminepenta(methylene phosphonic) acid | 0.2 | 0.3 | — | — | 0.2 | — | 0.2 | 0.3 |
| Hydroxyethane diphosphonic acid | — | — | 0.45 | — | — | 1.5 | — | 0.1 |

-continued

| Ingredient | Composition (wt % of composition) 1 | 2 | 3 | 4 | 5 | 6 | 7 | 8 |
|---|---|---|---|---|---|---|---|---|
| FWA | 0.1 | 0.2 | 0.1 | — | — | 0.2 | 0.05 | 0.1 |
| Solvents (1,2 propanediol, ethanol), stabilizers | 3 | 4 | 1.5 | 1.5 | 2 | 4.3 | 2 | 1.5 |
| Hydrogenated castor oil derivative structurant | 0.4 | 0.4 | 0.3 | 0.1 | 0.3 | — | 0.4 | 0.5 |
| Boric acid | 1.5 | 2.5 | 2 | 1.5 | 1.5 | 0.5 | 1.5 | 1.5 |
| Na formate | — | — | — | 1 | — | — | — | — |
| Reversible protease inhibitor[4] | — | — | 0.002 | — | — | — | — | — |
| Perfume | 0.5 | 0.7 | 0.5 | 0.5 | 0.8 | 1.5 | 0.5 | 0.8 |
| Perfume MicroCapsules slurry (30% am) | 0.2 | 0.3 | 0.7 | 0.2 | 0.05 | 0.4 | 0.9 | 0.7 |
| Ethoxylated thiophene Hueing Dye | | | | | | | 0.007 | 0.008 |
| Buffers (sodium hydroxide, Monoethanolamine) | To pH 8.2 | | | | | | | |
| Water and minors (antifoam, aesthetics) | To 100% | | | | | | | |

Examples 9-16

Liquid laundry detergent compositions suitable for top-loading automatic washing machines.

| Ingredient | Composition (wt % of composition) 9 | 10 | 11 | 12 | 13 | 14 | 15 | 16 |
|---|---|---|---|---|---|---|---|---|
| $C_{12-15}$ Alkylethoxy(1.8)sulfate | 20.1 | 15.1 | 20.0 | 15.1 | 13.7 | 16.7 | 10.0 | 9.9 |
| $C_{11.8}$ Alkylbenzene sulfonate | 2.7 | 2.0 | 1.0 | 2.0 | 5.5 | 5.6 | 3.0 | 3.9 |
| $C_{16-17}$ Branched alkyl sulfate | 6.5 | 4.9 | | 4.9 | 3.0 | 9.0 | 2.0 | |
| $C_{12-14}$ Alkyl-9-ethoxylate | 0.8 | 0.8 | 0.8 | 0.8 | 8.0 | 1.5 | 0.3 | 11.5 |
| $C_{12}$ dimethylamine oxide | | | 0.9 | | | | | |
| Citric acid | 3.8 | 3.8 | 3.8 | 3.8 | 3.5 | 3.5 | 2.0 | 2.1 |
| $C_{12-18}$ fatty acid | 2.0 | 1.5 | 2.0 | 1.5 | 4.5 | 2.3 | | 0.9 |
| Protease (Purafect ® Prime) | 1.5 | 1.5 | 0.5 | 1.5 | 1.0 | 1.8 | 0.5 | 0.5 |
| Amylase (Natalase ®) | 0.3 | 0.3 | 0.3 | 0.3 | 0.2 | 0.4 | | |
| Amylase (Stainzyme ®) | | | | | | | | 1.1 |
| Mannanase (Mannaway ®) | 0.1 | | | | | 0.1 | | |
| Pectate Lyase (Pectawash ®) | 0.1 | | | | | 0.2 | | |
| Xyloglucanase XYG1006* (mg aep/100 g detergent) | 5 | 13 | 2 | 5 | 20 | 1 | 2 | 3 |
| Borax | 3.0 | 3.0 | | | 2.0 | 3.0 | 3.0 | 3.3 |
| Na & Ca formate | 0.2 | 0.2 | | 0.2 | 0.2 | | 0.7 | |
| A compound having the following general structure: bis($(C_2H_5O)(C_2H_4O)n$)($CH_3$)—$N^+$—$C_xH_{2x}$—$N^+$—($CH_3$)-bis($(C_2H_5O)(C_2H_4O)n$), wherein n = from 20 to 30, and x = from 3 to 8, or sulphated or sulphonated variants thereof | 1.6 | 1.6 | 3.0 | 1.6 | 2.0 | 1.6 | 1.3 | 1.2 |
| Random graft co-polymer[1] | 0.4 | 0.2 | 1.0 | 0.5 | 0.6 | 1.0 | 0.8 | 1.0 |
| Diethylene triamine pentaacetic acid | 0.4 | 0.4 | 0.4 | 0.4 | 0.2 | 0.3 | 0.8 | |
| Tinopal AMS-GX | 0.2 | 0.2 | 0.2 | 0.2 | 0.2 | 0.3 | 0.1 | |
| Tinopal CBS-X | | | | | | 0.1 | | 0.2 |
| Amphiphilic alkoxylated grease cleaning polymer[3] | 1.0 | 1.3 | 1.3 | 1.4 | 1.0 | 1.1 | 1.0 | 1.0 |
| Texcare 240N (Clariant) | | | | 1.0 | | | | |
| Ethanol | 2.6 | 2.6 | 2.6 | 2.6 | 1.8 | 3.0 | 1.3 | |
| Propylene Glycol | 4.6 | 4.6 | 4.6 | 4.6 | 3.0 | 4.0 | 2.5 | |
| Diethylene glycol | 3.0 | 3.0 | 3.0 | 3.0 | 3.0 | 2.7 | 3.6 | |
| Polyethylene glycol | 0.2 | 0.2 | 0.2 | 0.2 | 0.1 | 0.3 | 0.1 | 1.4 |
| Monoethanolamine | 2.7 | 2.7 | 2.7 | 2.7 | 4.7 | 3.3 | 1.7 | 0.4 |
| Triethanolamine | | | | | | | | 0.9 |
| NaOH | to pH 8.3 | to pH 8.3 | to pH 8.3 | to pH 8.3 | to pH 8.3 | to pH 8.3 | to pH 8.3 | to pH 8.5 |

-continued

| Ingredient | Composition (wt % of composition) | | | | | | | |
|---|---|---|---|---|---|---|---|---|
| | 9 | 10 | 11 | 12 | 13 | 14 | 15 | 16 |
| Suds suppressor | | | | | | | | |
| Dye | 0.01 | 0.01 | 0.01 | | 0.01 | 0.01 | 0.01 | 0.0 |
| Perfume | 0.5 | 0.5 | 0.5 | 0.5 | 0.7 | 0.7 | 0.8 | 0.6 |
| Perfume MicroCapsules slurry (30% am) | 0.2 | 0.5 | 0.2 | 0.3 | 0.1 | 0.3 | 0.9 | 1.0 |
| Ethoxylated thiophene Hueing Dye | | | | | 0.002 | 0.004 | | |
| Water | balance | balance | balance | balance | balance | balance | balance | Balance |

Examples 17-22

The following are granular detergent compositions produced in accordance with the invention suitable for laundering fabrics.

| | 17 | 18 | 19 | 20 | 21 | 22 |
|---|---|---|---|---|---|---|
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 25 | 4 | 3 | 2 | |
| Zeolite | | 1 | | 1 | 4 | 1 |
| Silicate | 4 | 5 | 2 | 3 | 3 | 5 |
| Sodium Carbonate | 9 | 20 | 10 | 17 | 5 | 23 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Xyloglucanase XYG1006* (mg aep/100 g detergent) | 1.5 | 2.4 | 1.7 | 0.9 | 5.3 | 2.3 |
| Other enzymes powders | 0.23 | 0.17 | 0.5 | 0.2 | 0.2 | 0.6 |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Perfume MicroCapsules | 0.2 | 0.5 | 0.2 | 0.3 | 0.2 | 0.1 |
| Sulfate/Moisture/perfume | Balance to 100% | | | | | |

Examples 23-28

The following are granular detergent compositions produced in accordance with the invention suitable for laundering fabrics.

| | 23 | 24 | 25 | 26 | 27 | 28 |
|---|---|---|---|---|---|---|
| Linear alkylbenzenesulfonate with aliphatic carbon chain length $C_{11}$-$C_{12}$ | 8 | 7.1 | 7 | 6.5 | 7.5 | 7.5 |
| Other surfactants | 2.95 | 5.74 | 4.18 | 6.18 | 4 | 4 |
| Layered silicate | 2.0 | — | 2.0 | — | — | — |
| Zeolite | 7 | — | 2 | — | 2 | 2 |
| Citric Acid | 3 | 5 | 3 | 4 | 2.5 | 3 |
| Sodium Carbonate | 15 | 20 | 14 | 20 | 23 | 23 |
| Silicate | 0.08 | — | 0.11 | — | — | — |
| Soil release agent | 0.75 | 0.72 | 0.71 | 0.72 | — | — |
| Acrylic Acid/Maleic Acid Copolymer | 1.1 | 3.7 | 1.0 | 3.7 | 2.6 | 3.8 |
| Carboxymethyl cellulose (Finnfix BDA ex CPKelco) | 0.15 | — | 0.2 | — | 1 | — |
| Xyloglucanase XYG1006* (mg aep/100 g detergent) | 3.1 | 2.34 | 3.12 | 4.68 | 3.52 | 7.52 |
| Other enzyme powders | 0.65 | 0.75 | 0.7 | 0.27 | 0.47 | 0.48 |
| Bleach(es) and bleach activator(s) | 16.6 | 17.2 | 16.6 | 17.2 | 18.2 | 15.4 |
| Perfume MicroCapsules | 0.05 | 0.1 | 0.21 | 0.06 | 0.22 | 0.3 |
| Sulfate/Water & Miscellaneous | Balance to 100% | | | | | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2]Polyethylenimine (MW = 600) with 20 ethoxylate groups per —NH.

[3]Amphiphilic alkoxylated grease cleaning polymer is a polyethylenimine (MW = 600) with 24 ethoxylate groups per —NH and 16 propoxylate groups per —NH

[4]Reversible Protease inhibitor of structure:

-continued

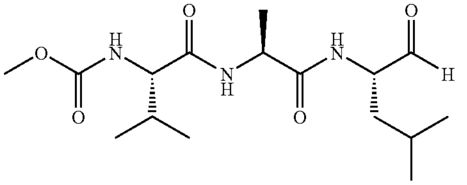 [SMILES: COC(=O)N[C@H](C(=O)N[C@@H](C)C(=O)N[C@H](C=O)CC(C)C)C(C)C]

*Remark: all enzyme levels expressed as % enzyme raw material, except for xyloglucanase where the level is given in mg active enzyme protein per 100 g of detergent.
XYG1006 enzyme is according to SEQ ID: 1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laundry detergent composition comprising:

(a) a glycosyl hydrolase having enzymatic activity towards both xyloglucan and amorphous cellulose substrates, wherein the glycosyl hydrolase belongs to glycosyl hydrolase family 44 or and has a sequence at least 90% homologous to sequence ID No. 1;

(b) a benefit agent containing delivery particle comprising a core material and a wall material that surrounds the core material, said particle's core material comprising a benefit agent, wherein said benefit agent comprises a perfume composition, said particle comprising, based on total particle weight, from about 20 weight % to about 95 weight % of said perfume composition, said particle's wall material comprising melamine crosslinked with formaldehyde, said particle having a Delivery Index of at least about 0.05 said composition being a consumer product; and (c) detersive surfactant.

2. A composition according to claim 1, wherein the glycosyl hydrolase enzyme has a sequence at least 95% homologous to sequence ID No. 1.

3. A composition according to claim 1, wherein the composition is in the form of a liquid.

4. A composition according to claim 1, wherein said particle has a Delivery Index of at least 7.

5. A composition according to claim 1, wherein said particle's core material further comprises a material selected from the group consisting of silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof.

6. A composition according to claim 1, wherein said perfume composition comprises a Quadrant III perfume raw material.

7. A composition according to claim 1, wherein said composition comprises, based on total composition weight, from about 0.2 to about 10 weight % of said particle.

8. A composition according to claim 1, wherein the composition comprises a material selected from the group consisting of calcium formate, formic acid, polyamines and mixtures thereof.

* * * * *

SEQUENCE LISTING

```
<160> NUMBER OF SEQ ID NOS: 1

<210> SEQ ID NO 1
<211> LENGTH: 524
<212> TYPE: PRT
<213> ORGANISM: Paenibacillus polyxyma

<400> SEQUENCE: 1

Val Val His Gly Gln Thr Ala Lys Thr Ile Thr Ile Lys Val Asp Thr
1               5                   10                  15

Phe Lys Asp Arg Lys Pro Ile Ser Pro Tyr Ile Tyr Gly Thr Asn Gln
            20                  25                  30

Asp Leu Ala Gly Asp Glu Asn Met Ala Ala Arg Arg Leu Gly Gly Asn
        35                  40                  45

Arg Met Thr Gly Tyr Asn Trp Glu Asn Asn Met Ser Asn Ala Gly Ser
    50                  55                  60

Asp Trp Gln Gln Ser Ser Asp Asn Tyr Leu Cys Ser Asn Gly Gly Leu
65                  70                  75                  80

Thr Gln Ala Glu Cys Glu Lys Pro Gly Ala Val Thr Thr Ser Phe His
                85                  90                  95

Asp Gln Ser Leu Lys Leu Gly Thr Tyr Ser Leu Val Thr Leu Pro Met
            100                 105                 110

Ala Gly Tyr Val Ala Lys Asp Gly Asn Gly Ser Val Gln Glu Ser Glu
        115                 120                 125

Lys Ala Pro Ser Ala Arg Trp Asn Gln Val Val Asn Ala Lys Asn Ala
    130                 135                 140

Pro Phe Gln Leu Gln Pro Asp Leu Asn Asp Asn Arg Val Tyr Val Asp
145                 150                 155                 160

Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190
```

-continued

```
His Thr His Pro Arg Ile His Gly Glu Lys Val Gly Ala Lys Glu Leu
        195                 200                 205

Val Asp Arg Ser Val Ser Leu Ser Lys Ala Val Lys Ala Ile Asp Ala
    210                 215                 220

Gly Ala Glu Val Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Ser Gln Val
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
    290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Asn Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
        355                 360                 365

Gly Gly Ile Ala Met Thr Asp Val Leu Gly Ile Leu Gly Lys Asn Asp
    370                 375                 380

Val Tyr Met Ala Asn Tyr Trp Lys Leu Lys Asp Gly Val Asn Asn Tyr
385                 390                 395                 400

Val Ser Ala Ala Tyr Lys Leu Tyr Arg Asn Tyr Asp Gly Lys Asn Ser
                405                 410                 415

Thr Phe Gly Asp Thr Ser Val Ser Ala Gln Thr Ser Asp Ile Val Asn
            420                 425                 430

Ser Ser Val His Ala Ser Val Thr Asn Ala Ser Asp Lys Glu Leu His
        435                 440                 445

Leu Val Val Met Asn Lys Ser Met Asp Ser Ala Phe Asp Ala Gln Phe
    450                 455                 460

Asp Leu Ser Gly Ala Lys Thr Tyr Ile Ser Gly Lys Val Trp Gly Phe
465                 470                 475                 480

Asp Lys Asn Ser Ser Gln Ile Lys Glu Ala Ala Pro Ile Thr Gln Ile
                485                 490                 495

Ser Gly Asn Arg Phe Thr Tyr Thr Val Pro Pro Leu Thr Ala Tyr His
            500                 505                 510

Ile Val Leu Thr Thr Gly Asn Asp Thr Ser Pro Val
        515                 520
```